US012741973B2

(12) United States Patent
Zhang

(10) Patent No.: US 12,741,973 B2
(45) **Date of Patent: *Sep. 22, 2026**

(54) SOLID FORMS OF 3-(5-FLUOROBENZOFURAN-3-YL)-4-(5-METHYL-5H-[1,3]DIOXOLO[4,5-F] INDOL-7-YL)PYRROLE-2,5-DIONE

(71) Applicant: Actuate Therapeutics Inc., Fort Worth, TX (US)

(72) Inventor: Yamin Zhang, Beijing (CN)

(73) Assignee: Actuate Therapeutics Inc., Fort Worth, TX (US)

( * ) Notice: Subject to any disclaimer, the term of this patent is extended or adjusted under 35 U.S.C. 154(b) by 159 days.

This patent is subject to a terminal disclaimer.

(21) Appl. No.: 18/830,117

(22) Filed: Sep. 10, 2024

(65) Prior Publication Data

US 2025/0115615 A1 Apr. 10, 2025

Related U.S. Application Data

(63) Continuation of application No. 17/855,847, filed on Jul. 1, 2022, now Pat. No. 12,116,374, which is a continuation of application No. 16/755,903, filed as application No. PCT/US2018/056083 on Oct. 16, 2018, now Pat. No. 11,407,759.

(60) Provisional application No. 62/572,603, filed on Oct. 16, 2017.

(51) Int. Cl.
*C07D 491/056* (2006.01)

(52) U.S. Cl.
CPC ...... *C07D 491/056* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 8,207,216 B2 | 6/2012 | Kozikowski et al. |
| 11,136,334 B2 | 10/2021 | Zhang |
| 11,407,759 B2 | 8/2022 | Zhang |
| 2022/0009939 A1 | 1/2022 | Zhang |

FOREIGN PATENT DOCUMENTS

| | | |
|---|---|---|
| BR | 112020002892 A2 | 8/2020 |
| WO | WO 2008/077138 A1 | 6/2008 |
| WO | WO 2019/032958 A1 | 2/2019 |

OTHER PUBLICATIONS

Gaisina, et al., "From a Natural Product Lead to the Identification of Potent and Selective Benzofuran-3-yl-(indol-3- yl)maleimides as Glycogen Synthase Kinase 3B Inhibitors That Suppress Proliferation and Survival of Pancreatic Cancer Cells", J. Med. Chem., 2009, vol. 52, pp. 1853-1863.
Pal, et al., "Inhibition of GSK-3 Induces Differentiation and Impaired Metabolism in Renal Cancer, Molecular Cancer Therapeutics", vol. 13, No. 2, pp. 285-296, Dec. 10, 2013.
Hilliard, et al., "Glycogen Synthase Kinase 3B Inhibitors Induce Apoptosis in Ovarian Cancer Cells and Inhibit In Vivo Tumor Growth," Anti Cancer Drugs, vol. 22, pp. 978-985, 2011.
Caira, et al., "Crystalline Polymorphism of Organic Compounds", Topics in Current Chemistry, vol. 198, pp. 163-208, Jan. 1, 1998.
Baumgart, et al., "GSK-3B Governs Inflammation-Induced NFATc2 Signaling Hubs to Promote Pancreatic Cancer Progression", American Association for Cancer Research, pp. 491-502, Jan. 28, 2016.
Decision on Rejection issued in Japanese Patent Application No. 2020-521319 dated May 16, 2023, with English translation.
Cains; "Classical Methods of Preparation of Polymorphs and Alternative Solid Forms"; Polymorphism in Pharmaceutical Solids; Drugs and the Pharmaceutical Sciences; vol. 192; Ch.4; pp. 76-80, 123-130; 2009.
European Patent Office, Extended European Search Report for EP Application No. 25225740.7, dated Jun. 22, 2026.

*Primary Examiner* — Brian J Davis
(74) *Attorney, Agent, or Firm* — Lisa Mueller; Casimir Jones SC

(57) ABSTRACT

The present disclosure relates to Solid Forms of 3-(5-Fluorobenzofuran-3-yl)-4-(5-methyl-5H-[1,3]dioxolo[4,5-f] indol-7-yl)pyrrole-2,5-dione, processes for preparation thereof, pharmaceutical compositions thereof, and uses thereof in treating disease.

17 Claims, 4 Drawing Sheets

SOLID FORMS OF 3-(5-FLUOROBENZOFURAN-3-YL)-4-(5-METHYL-5H-[1,3]DIOXOLO[4,5-F]INDOL-7-YL)PYRROLE-2,5-DIONE

CROSS-REFERENCE TO RELATED APPLICATION

The application claims the benefit of priority to U.S. Provisional Application No. 62/572,603, filed on Oct. 16, 2017, the entirety of which is incorporated by reference herein.

FIELD OF THE DISCLOSURE

The present disclosure relates to solid forms of 3-(5-Fluorobenzofuran-3-yl)-4-(5-methyl-5H-[1,3]dioxolo[4,5-f]indol-7-yl)pyrrole-2,5-dione, processes for preparation thereof, pharmaceutical compositions thereof, and uses thereof in treating disease.

BACKGROUND OF THE DISCLOSURE 3-(5-Fluorobenzofuran-3-yl)-4-(5-methyl-5H-[1,3]dioxolo[4,5-f]indol-7-yl) pyrrole-2,5-dione ("9-ING-41") has the following chemical structure:

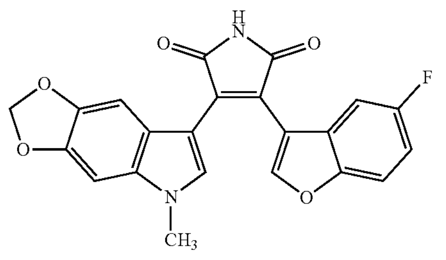 [SMILES: Cn1cc(C2=C(c3coc4ccc(F)cc34)C(=O)NC2=O)c2cc3c(cc21)OCO3]

9-ING-41 has been reported as being useful for the treatment of cancers, including brain, lung, breast, ovarian, bladder, neuroblastoma, renal, and pancreatic cancers, as well as for treatment of traumatic brain injury.

The structure, properties, and/or biological activity of 9-ING-41 are set forth in U.S. Pat. No. 8,207,216; Gaisina et al., From a Natural Product Lead to the Identification of Potent and Selective Benzofuran-3-yl-(indol-3-yl) maleimides as Glycogen Synthase Kinase 3β Inhibitors That Suppress Proliferation and Survival of Pancreatic Cancer Cells, *J. Med. Chem.* 2009, 52, 1853-1863; and Hilliard, et al., Glycogen synthase kinase 3β inhibitors induce apoptosis in ovarian cancer cells and inhibit in-vivo tumor growth, *Anti-Cancer Drugs* 2011, 22:978-985.

There is a need for novel solid forms (including polymorphs and solvates) of 9-ING-41.

SUMMARY OF THE DISCLOSURE

The present disclosure relates to solid forms of 9-ING-41, processes for preparing solid forms of 9-ING-41, pharmaceutical compositions comprising solid forms of 9-ING-41, and methods of treatment comprising administering solid forms of 9-ING-41.

In some aspects, the present disclosure is directed to a solid form which is crystalline Form II of 3-(5-fluorobenzofuran-3-yl)-4-(5-methyl-5H-[1,3]dioxolo[4,5-f]indol-7-yl) pyrrole-2,5-dione ("9-ING-41").

The present disclosure also provides processes for preparing solid forms of 9-ING-41.

The present disclosure also provides pharmaceutical compositions comprising the solid forms of 9-ING-41.

The present disclosure also provides methods of treating disease comprising administering to a patient in need thereof a therapeutically effective amount of a disclosed solid form of 9-ING-41.

DETAILED DESCRIPTION OF THE INVENTION

Figure 1:
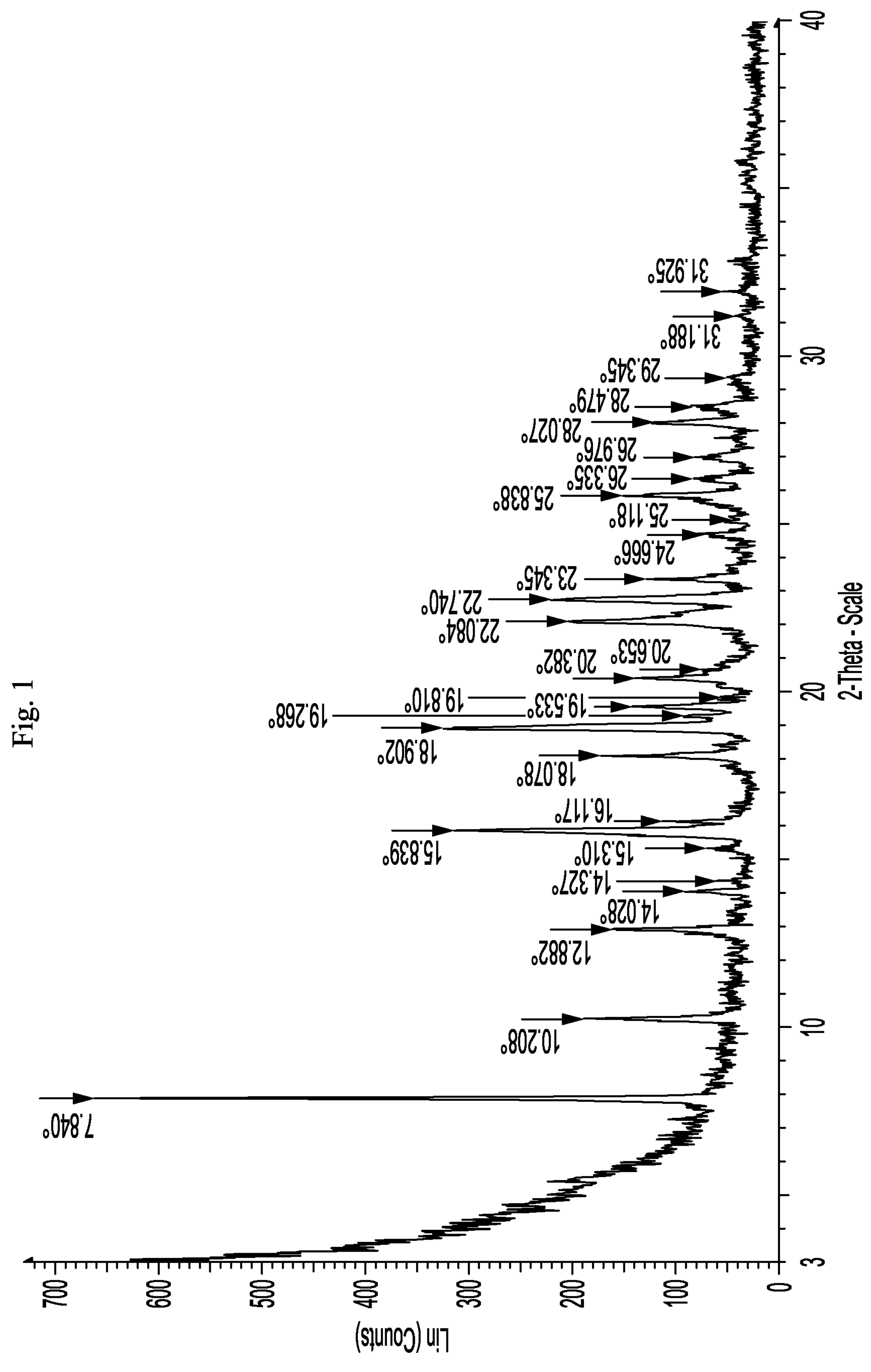
FIG. 1 shows an X-ray powder diffractogram (XRPD) of Form II of 9-ING-41.

The present disclosure relates to solid forms of 9-ING-41, processes for preparation thereof and pharmaceutical compositions comprising the solid state form(s). The disclosure also relates to the conversion of the described solid state forms of 9-ING-41 to other solid state forms of 9-ING-41, 9-ING-41 salts and their solid state forms thereof.

The name "9-ING-41" is another name for 3-(5-Fluorobenzofuran-3-yl)-4-(5-methyl-5H-[1,3]dioxolo[4,5-f]indol-7-yl)pyrrole-2,5-dione, and the two names are used interchangeably herein.

The solid state forms of 9-ING-41 according to the present disclosure may have advantageous properties selected from at least one of: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents and advantageous processing and handling characteristics such as compressibility, or bulk density.

A crystal form may be referred to herein as being characterized by graphical data "as shown in" or "as characterized by" a Figure. Such data include, for example, powder X-ray diffractograms (XRPD), Differential Scanning Calorimetry (DSC) thermograms, thermogravimetric analysis (TGA) profiles, and differential vapor sorption profiles (DVS). As is well-known in the art, the graphical data potentially provides additional technical information to further define the respective solid state form which can not necessarily be described by reference to numerical values or peak positions alone. Thus, the term "substantially as shown in" when referring to graphical data in a Figure herein means a pattern that is not necessarily identical to those depicted herein, but that falls within the limits of experimental error or deviations, when considered by one of ordinary skill in the art. The skilled person would readily be able to compare the graphical data in the Figures herein with graphical data generated for an unknown crystal form and confirm whether the two sets of graphical data are characterizing the same crystal form or two different crystal forms.

A solid, crystalline form may be referred to herein as "polymorphically pure" or as "substantially free of any other form." As used herein in this context, the expression "substantially free of any other forms" will be understood to mean that the solid form contains about 20% or less, about 10% or less, about 5% or less, about 2% or less, about 1% or less, or 0% of any other forms of the subject compound as measured, for example, by XRPD. Thus, a solid form of 9-ING-41 described herein as substantially free of any other solid forms would be understood to contain greater than about 80% (w/w), greater than about 90% (w/w), greater than about 95% (w/w), greater than about 98% (w/w), greater than about 99% (w/w), or about 100% of the subject solid form of 9-ING-41. Accordingly, in some embodiments of the disclosure, the described solid forms of 9-ING-41 may contain from about 1% to about 20% (w/w), from about 5% to about 20% (w/w), or from about 5% to about 10% (w/w) of one or more other solid forms of 9-ING-41.

As used herein, unless stated otherwise, XRPD peaks reported herein are measured using $CuK_\alpha$ radiation, $\lambda$=1.5419 Å.

The modifier "about" should be considered as disclosing the range defined by the absolute values of the two endpoints. For example, the expression "from about 2 to about 4" also discloses the range "from 2 to 4." When used to modify a single number, the term "about" refers to plus or minus 10% of the indicated number and includes the indicated number. For example, "about 10%" indicates a range of) % to 11%, and "about 1" means from 0.9-1.1.

The term "solvate", as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

In some aspects, the present disclosure pertains to solid forms of 9-ING-41.

In some aspects of the present disclosure, the solid form of 9-ING-41 is crystalline Form II of 9-ING-41. In other aspects, the solid form is crystalline Form II of 9-ING-41 substantially free of any other solid form of 9-ING-41. Crystalline Form II of 9-ING-41 exhibits an XRPD substantially as shown in FIG. 1.

The XRPD of crystalline Form II of 9-ING-41 shown in FIG. 1 comprises reflection angles (degrees 2-theta±0.2 degrees 2-theta) as shown in Table 1:

TABLE 1

| XRPD Data for Form II Angle (degrees 2-theta ± 0.2 degrees 2-theta) |
|---|
| 7.840 |
| 10.208 |
| 12.882 |
| 14.028 |
| 14.327 |
| 15.310 |
| 15.839 |
| 16.117 |
| 18.078 |
| 18.902 |
| 19.268 |
| 19.533 |
| 19.810 |
| 20.382 |
| 20.653 |
| 22.084 |
| 22.740 |
| 23.345 |
| 24.666 |
| 25.118 |
| 25.838 |
| 26.335 |
| 26.976 |
| 28.027 |
| 28.479 |
| 29.345 |
| 31.188 |
| 31.925 |

In some embodiments of the present disclosure, crystalline Form II of 9-ING-41 is characterized by an XRPD pattern comprising a peak at one of the angles listed in Table 1. In other aspects, crystalline Form II of 9-ING-41 is characterized by an XRPD pattern comprising more than one peak at one of the angles listed in Table 1 above. In other aspects, crystalline Form II of 9-ING-41 is characterized by an XRPD pattern comprising two peaks selected from the angles listed in Table 1 above. In other aspects, crystalline Form II of 9-ING-41 is characterized by an XRPD pattern comprising three peaks selected from the angles listed in Table 1 above. In other aspects, crystalline Form II of 9-ING-41 is characterized by an XRPD pattern comprising four peaks selected from the angles listed in Table 1 above. In other aspects, crystalline Form II of 9-ING-41 is characterized by an XRPD pattern comprising five peaks selected from the angles listed in Table 1 above. In other aspects, crystalline Form II of 9-ING-41 is characterized by an XRPD pattern comprising six peaks selected from the angles listed in Table 1 above. In other aspects, crystalline Form II of 9-ING-41 is characterized by an XRPD pattern comprising seven peaks selected from the angles listed in Table 1 above. In other aspects, crystalline Form II of 9-ING-41 is characterized by an XRPD pattern comprising eight peaks selected from the angles listed in Table 1 above. In other aspects, crystalline Form II of 9-ING-41 is characterized by an XRPD pattern comprising nine peaks selected from the angles listed in Table 1 above. In other aspects, crystalline Form II of 9-ING-41 is characterized by an XRPD pattern comprising ten peaks selected from the angles listed in Table 1 above. In other aspects, crystalline Form II of 9-ING-41 is characterized by an XRPD pattern comprising more than ten peaks selected from the angles listed in Table 1 above.

In some embodiments, crystalline Form II of 9-ING-41 is characterized by an XRPD pattern comprising a peak at 7.8 degrees±0.2 degrees 2-theta. In other embodiments, crystalline Form II of 9-ING-41 is characterized by an XRPD pattern comprising peaks at 7.8, 12.9, 15.8, and 18.9 degrees±0.2 degrees 2-theta. In other embodiments, crystalline Form II of 9-ING-41 is characterized by an XRPD pattern comprising peaks at 12.9, 18.1, 28.0, and 28.5 degrees±0.2 degrees 2-theta.

In some embodiments of the present disclosure, crystalline Form II of 9-ING-41 is characterized by an XRPD pattern comprising peaks at three or more of 7.8, 12.9, 15.8, 18.1, 18.9, 19.5, 22.1, 22.7, 28.0, and 28.5±0.2 degrees 2-theta. In some embodiments of the present disclosure, crystalline Form II of 9-ING-41 is characterized by an XRPD pattern comprising peaks at four or more of 7.8, 12.9, 15.8, 18.1, 18.9, 19.5, 22.1, 22.7, 28.0, and 28.5, degrees±0.2 degrees 2-theta. In some embodiments of the present disclosure, crystalline Form II of 9-ING-41 is characterized by an XRPD pattern comprising peaks at five or more of 7.8, 12.9, 15.8, 18.1, 18.9, 19.5, 22.1, 22.7, 28.0, and 28.5, degrees±0.2 degrees 2-theta. In some embodiments of the present disclosure, crystalline Form II of 9-ING-41 is characterized by an XRPD pattern comprising peaks at six or more of 7.8, 12.9, 15.8, 18.1, 18.9, 19.5, 22.1, 22.7, 28.0, and 28.5, degrees±0.2 degrees 2-theta. In some embodiments of the present disclosure, crystalline Form II of 9-ING-41 is characterized by an XRPD pattern comprising peaks at seven or more of 7.8, 12.9, 15.8, 18.1, 18.9, 19.5, 22.1, 22.7, 28.0, and 28.5, degrees±0.2 degrees 2-theta.

Figure 2:
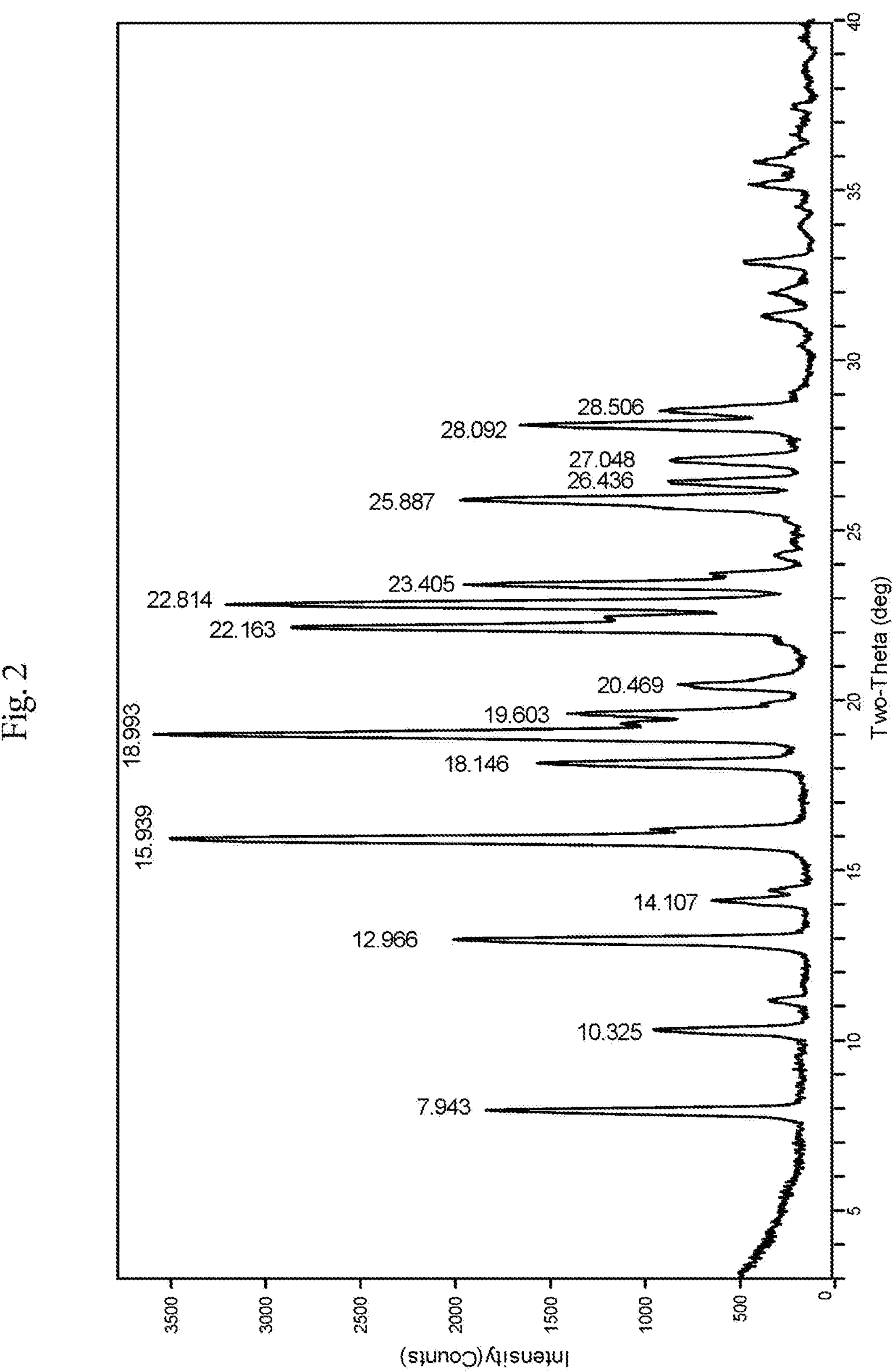
FIG. 2 shows an X-ray powder diffractogram (XRPD) of Form II of 9-ING-41.

In some embodiments, crystalline Form II of 9-ING-41 exhibits an XRPD pattern substantially as shown in FIG. 2.

Figure 3:
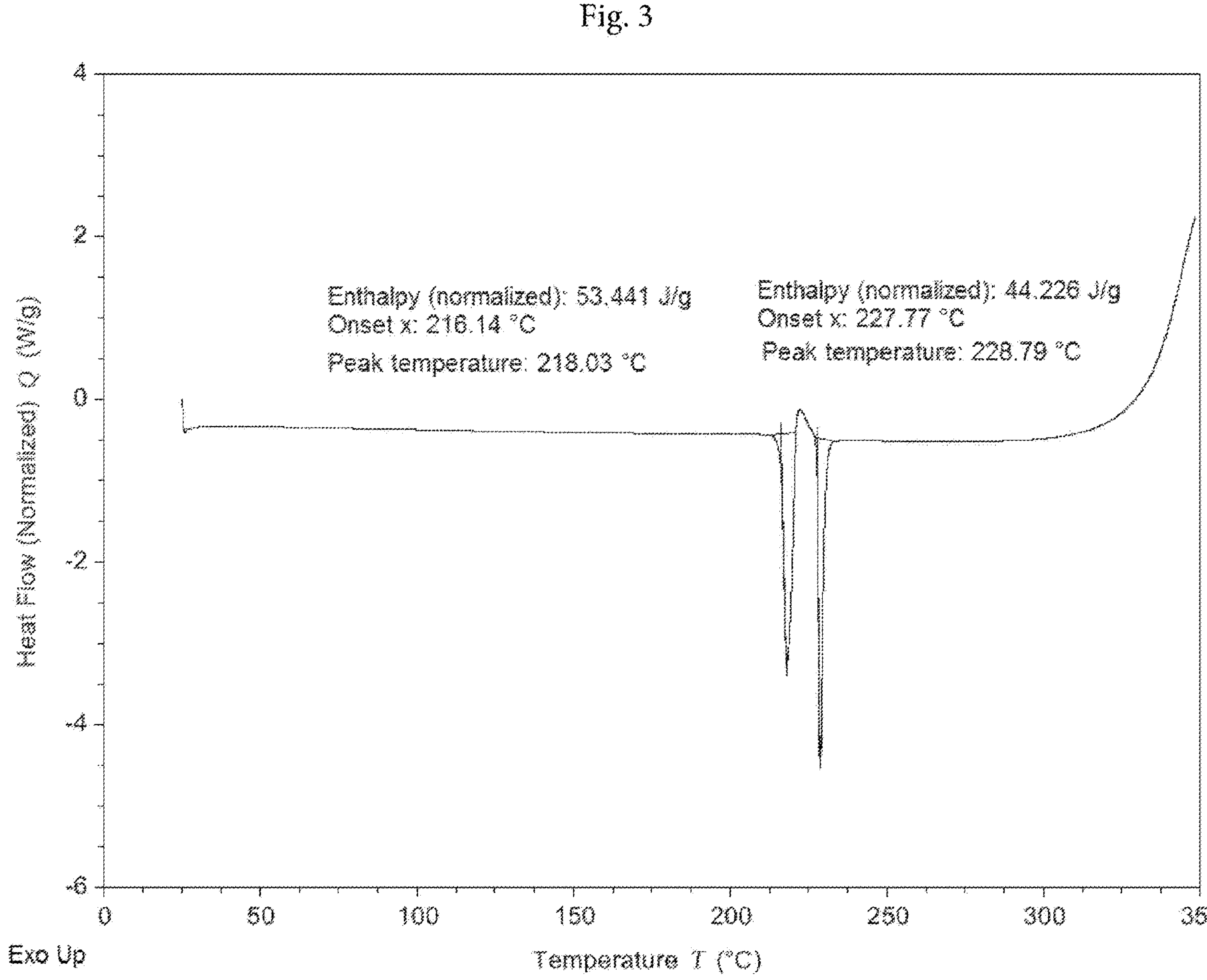
FIG. 3 shows a differential scanning calorimetry (DSC) profile of Form II of 9-ING-41.

Crystalline Form II of 9-ING-41 can be characterized by a DSC thermogram substantially as shown in FIG. 3. As FIG. 3 shows, crystalline Form II of 9-ING-41 produced an endothermic peak at 218.03° C., with a peak onset temperature of 216.14° C., and an enthalpy of melting of 53.441 J/g, when heated at a rate of 10° C./min. In some embodiments of the present disclosure, crystalline Form II of 9-ING-41 is characterized by a DSC thermogram comprising an endothermic peak at about 218° C. In other embodiments of the present disclosure, crystalline Form II of 9-ING-41 is characterized by a DSC enthalpy of melting of about 53 J/g.

Figure 4:
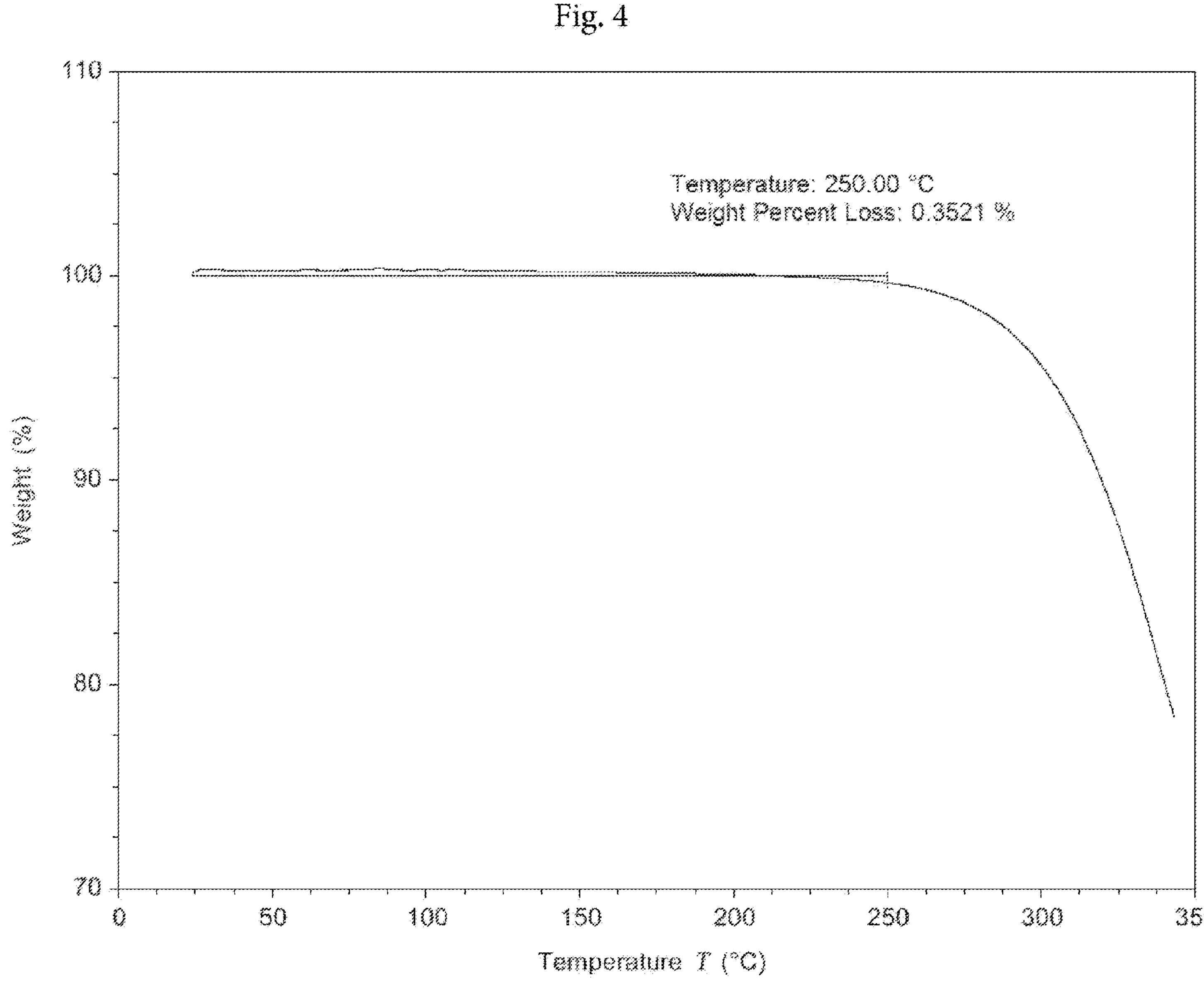
FIG. 4 shows a thermogravimetric analysis (TGA) profile of Form II of 9-ING-41.

Crystalline Form II of 9-ING-41 can be characterized by a TGA profile substantially as shown in FIG. 4 when heated at a rate of 10° C./min. As FIG. 4 shows, crystalline Form II of 9-ING-41 lost about 0.3521% of its weight upon heating between about 150° C. and about 250° C. when heated at a rate of 10° C./min.

In some embodiments of the present disclosure, crystalline Form II of 9-ING-41 is characterized by an XRPD pattern comprising peaks at 7.8, 12.9, 15.8, 18.1, 18.9, 19.5, 22.1, 22.7, 28.0, and 28.5±0.2 degrees 2-theta, and a DSC thermogram comprising an endothermic peak at about 218° C. when heated at a rate of 10° C./min.

In some aspects, the present disclosure pertains to processes for preparing the disclosed solid forms of 9-ING-41. In some aspects, the process comprises concentrating a solution of 9-ING-41 dissolved in a solvent or mixture of solvents.

In some aspects, the present disclosure pertains to processes for preparing crystalline Form II of 9-ING-41. In some embodiments, the process comprises the step of concentrating (e.g., in vacuo or via evaporation) a solution of 9-ING-41 dissolved in a mixture of 3-methyl-butanol/acetone in a ratio of volumes of about 1:1. In other embodiments, the process comprises the step of cooling a warm (i.e., greater than 25° C.) solution of 9-ING-41 dissolved in a mixture of isoamyl alcohol:acetonitrile in a ratio of volumes of about 10:1.

In another aspect, the present disclosure encompasses pharmaceutical compositions comprising a solid form of 9-ING-41 of the present disclosure and at least one pharmaceutically acceptable excipient. Pharmaceutically acceptable excipients will be known to those of skill in the art. The pharmaceutical compositions may be administered in any convenient dosage form. Representative dosage forms include tablets, capsules, caplets, reconstitutable powders, elixirs, liquids, colloidal or other types of suspensions, emulsions, beads, beadlets, granules, microparticles, nanoparticles, and combinations thereof. The amount of composition administered will be dependent on the subject being treated, the subject's weight, the severity of the condition being treated, the manner of administration, and the judgment of the prescribing physician. In some embodiments, the pharmaceutical composition comprises crystalline Form II of 9-ING-41 and at least one pharmaceutically acceptable excipient.

The present disclosure also encompasses sterile aqueous or organic solution formulations of 9-ING-41 in which the formulation is prepared from a solid form of 9-ING-41 of the present disclosure. Thus, in some aspects, the present disclosure comprises a process of preparing a pharmaceutical composition that is a solution comprising 9-ING-41. In some embodiments, the method of preparing a pharmaceutical composition comprising a solution of 9-ING-41 comprises dissolving a solid form of 9-ING-41 of the present disclosure in a solvent or mixture of solvents. In some embodiments, the method comprises dissolving crystalline Form II of 9-ING-41 in an aqueous solvent, a non-aqueous solvent, or a mixture of aqueous and/or non-aqueous solvents. The aqueous solvent, non-aqueous solvent, or mixture of aqueous and/or non-aqueous solvents in the embodiments may contain other dissolved ingredients, such as for example, polyethylene glycols, benzyl alcohol, polysorbates, tocopheryl polyethylene glycol succinates, as well as other surfactants, solubilizers, or other pharmaceutically acceptable excipients. In other embodiments, the process comprises dissolving 9-ING-41 crystalline Form II in an aqueous solvent.

The solid state forms of 9-ING-41 as defined herein, as well as the pharmaceutical compositions or formulations thereof, can be used as medicaments, particularly for the treatment of cancer, including brain, lung, breast, ovarian, bladder, neuroblastoma, renal, and pancreatic cancers, as well as for treatment of traumatic brain injury.

Having described the disclosure with reference to certain preferred embodiments, other embodiments will become apparent to one skilled in the art from consideration of the specification. The disclosure is further illustrated by reference to the following examples. It will be apparent to those skilled in the art that many modifications, both to materials and methods, may be practiced without departing from the scope of the disclosure.

Analytical Methods

XRPD Analysis

XRPD analyses were performed using an X-ray diffractometer (Bruker D8 advance) equipped with LynxEye detector. The instrument parameters were listed below.

Scan: 3° (2θ) to 40° (2θ)

Increment: 0.02° (2θ)

Scan speed: 0.3 sec/step

Voltage: 40 KV

Current: 40 mA

Rotation: On

Sample hold: Zero-background sample holder

The D2 phaser X-ray power diffractometer (Bruker) of samples were scanned from 3 to 40° 2θ, at a step of 0.02° 2θ. The tube voltage and current were 30 KV and 10 mA, respectively.

TGA Analysis

TGA analyses were be carried out on a TA Instruments TGA Q500 or Discovery TGA 55 (TA Instruments, US). Samples were placed in a tarred open aluminum pan and heated from room temperature to the final temperature at a rate of 10° C./min.

DSC Analysis

DSC analysis was conducted with DSC Q200 or Discovery DSC 250 (TA Instruments, US). A weighted sample was placed into a DSC pinhole pan, and the weight was accurately recorded. The sample was heated at 10° C./min to the final temperature.

DVS Analysis

DVS analyses can be conducted on an IGAsorp (HidenIsochema Ltd.). For an isotherm test, the chamber temperature can be maintained by a water bath at constant 25.0±1.0° C.

Polarized Light Microscope (PLM)

PLM analysis was conducted with a polarized light microscope ECLIPSE LV100POL (Nikon, JPN).

HPLC Analysis

Instrument: Agilent 1260 Infinity Series
Diluent: Acetonitrile
Flow rate: 1.5 mL/min
Mobile phase: A: 0.05% TFA in water; B: 0.05% TFA in Acetonitrile
Injection volume: 1 μl.
Column: XDB-C18, 4.6*50 mm, 1.8 μm
Column Temperature: 40° C.
Detection: 220 nm
Run Time: 8 minutes (2 minutes delay for next injection)
Gradient (T/B %): 0.0/30, 6.0/100, 8.0/100

EXAMPLES

Example 1: Preparation of 9-ING-41

Crude 9-ING-41 can be obtained by the general methods described in U.S. Pat. No. 8,207,216, and in Gaisina et al., From a Natural Product Lead to the Identification of Potent and Selective Benzofuran-3-yl-(indol-3-yl) maleimides as Glycogen Synthase Kinase 3β Inhibitors That Suppress Proliferation and Survival of Pancreatic Cancer Cells, *J. Med. Chem.* 2009, 52, 1853-1863.

Example 2: Preparation of 9-ING-41 Crystalline Form I

Crystalline Form I of 9-ING-41 may also be prepared as follows.

Synthesis of Intermediate 1

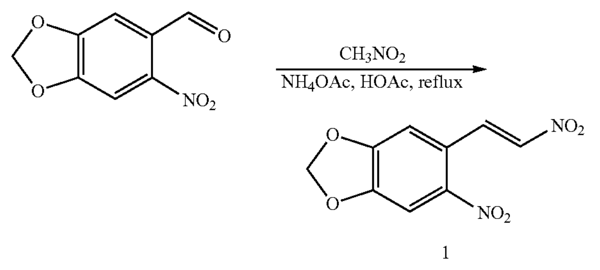

1

Into a 3-L 4-necked round-bottom flask, purged and maintained with an inert atmosphere of nitrogen, was placed 6-nitro-2H-1,3-benzodioxole-5-carbaldehyde (200 g, 1.02 mol, 1.00 equiv), ammonium acetate (200 g, 2.59 mol, 2.53 equiv), acetic acid (2 L), and nitromethane (313 g, 5.13 mol, 5.00 equiv). The solution was stirred for 12 h at 100° C. The reaction repeated three times. The solutions were combined and diluted with 20 L of water. The resulting solution was extracted with 3×10 L of ethyl acetate and the organic layers were combined. The mixture was washed with 3×10 L of brine, dried over anhydrous sodium sulfate and concentrated under vacuum. This resulted in 450 g (crude) of 5-nitro-6-[(E)-2-nitroethenyl]-2H-1, 3-benzodioxole (1) as a dark green solid.

Synthesis of Intermediate 2

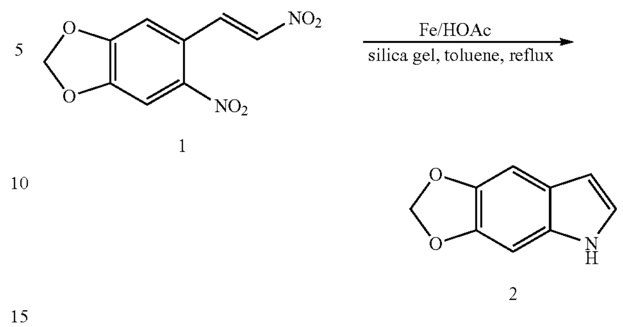

1

2

Fe (120 g, 2.14 mol, 17.01 equiv) was slowly added in portions into a suspension of 5-nitro-6-[(Z)-2-nitroethenyl]-2H-1,3-benzodioxole (30 g, 125.97 mmol, 1.00 equiv), silica gel (120 g) in acetic acid (300 mL), toluene (200 mL), and cyclohexane (400 mL) at 80° C. under nitrogen. The resulting black mixture was stirred for 8 h at 80° C. The reaction repeated ten times. The reaction mixtures were combined. The solids were filtrated out. The filtrate was concentrated under vacuum and the residue was applied onto a silica gel column with ethyl acetate/petroleum ether (1/5). The collected fractions were combined and concentrated under vacuum to give 67.3 g (33%) of 2H, 5H-[1,3] dioxolo [4,5-f] indole (2) as an off-white solid.

Synthesis of Intermediate 3

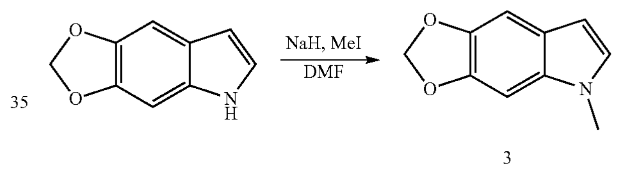

3

Sodium hydride (19.9 g, 497.50 mmol, 1.18 equiv. 60%) was added in portions into a solution of 2H,3H,5H-furo[2,3-f]indole (67.3 g, 422.78 mmol, 1.00 equiv) in N,N-dimethylformamide (1.3 L) at 0° C. under nitrogen. The mixture was stirred for 1 h at 0° C. and $CH_3I$ (70.9 g, 499.51 mmol, 1.18 equiv) was added dropwise. The resulting solution was stirred for 3 h at room temperature. The solution was quenched by added 1 L of ice water. The resulting solution was extracted with 3×1 L of ethyl acetate and the organic layers were combined. The mixture was washed with 3×1 L of brine, dried over anhydrous sodium sulfate and concentrated under vacuum. The residue was applied onto a silica gel column with ethyl acetate/petroleum ether (1/10). The collected fractions were combined and concentrated under vacuum to give 71 g (97%) of 5-methyl-2H, 3H,5H-furo[2,3-f]indole (3) as a light yellow solid.

Synthesis of Intermediate 4

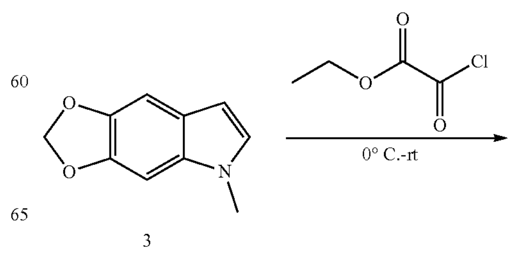

3

-continued

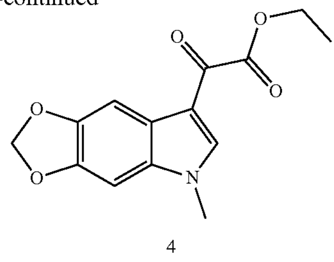

4

Ethyl 2-chloro-2-oxoacetate (220 g, 1.61 mol, 3.96 equiv) was added dropwise into a solution of 5-methyl-2H,3H,5H-furo[2,3-f]indole (70.4 g, 406.44 mmol, 1.00 equiv) in ethyl ether (1.6 L) at 0° C. under nitrogen. The resulting solution was warmed to room temperature and stirred for 4 h. The reaction was quenched slowly by the addition of 2 L of ice water and the pH value of the resulting solution was adjusted to 9 by Na2CO3. The resulted mixture was extracted with 3×1.5 L of ethyl acetate. The organic layers were combined and dried over anhydrous sodium sulfate and concentrated under vacuum to give 92.8 g (84%) of ethyl 2-[5-methyl-2H,3H,5H-furo[2,3-f]indol-7-yl]-2-oxoacetate (4) as a light yellow solid.

1H NMR (300 MHz, DMSO-d6): β8.28 (s, 4H), 7.56 (s, 4H), 7.27 (s, 4H), 6.17 (s, 1H), 6.08 (s, 8H), 4.35 (q, J=7.1 Hz, 7H), 3.85 (s, 11H), 3.35 (s, 2H), 1.35 (t, J=7.1 Hz, 11H), 1.25 (s, 2H).

Synthesis of Intermediate 5

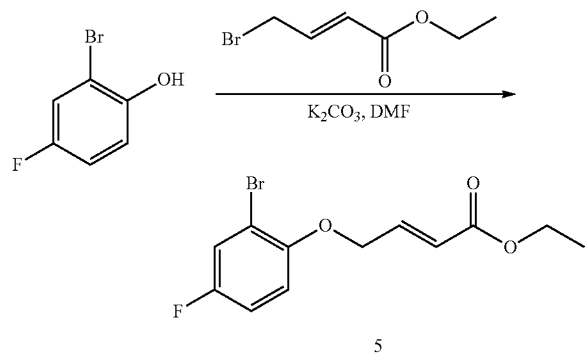

5

Into a 10-L 4-necked round-bottom flask was placed 2-bromo-4-fluorophenol (500 g, 2.62 mol, 1.00 equiv), N,N-dimethylformamide (5 L), potassium carbonate (1253 g, 9.07 mol, 3.46 equiv), and ethyl (2E)-4-bromobut-2-enoate (1010 g, 5.23 mol, 2.00 equiv). The resulting solution was stirred for 12 h at room temperature. The solids were collected by filtration. The reaction was then quenched by the addition of 15 L of water and extracted with 3×10 L of ethyl acetate. The organic layers were combined and washed with 4×20 L of brine. The mixture was dried over anhydrous sodium sulfate and concentrated under vacuum. The residue was applied onto a silica gel column with ethyl acetate/petroleum ether (1/20). The collected fractions were combined and concentrated under vacuum to give 500 g (63%) of ethyl (2E)-4-(2-bromo-4-fluorophenoxy)but-2-enoate (5) as a white solid.

Synthesis of Intermediate 6

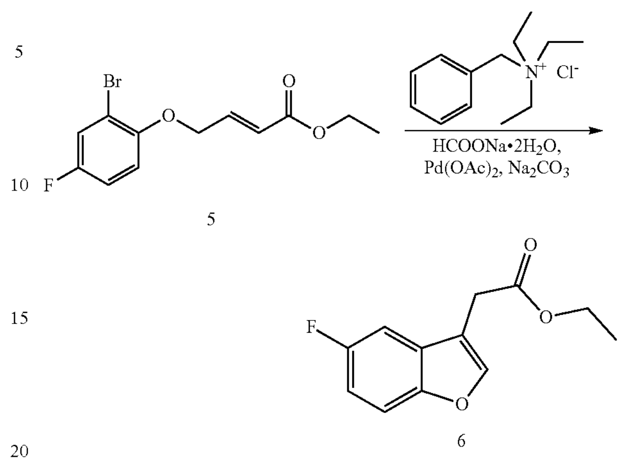

5

6

Into a 2-L 3-necked round-bottom flask, purged and maintained with an inert atmosphere of nitrogen, was placed ethyl (2E)-4-(2-bromo-4-fluorophenoxy)but-2-enoate (125 g, 412.37 mmol, 1.00 equiv), benzyltriethylazanium chloride (99 g, 434.64 mmol, 1.05 equiv), sodium formate dihydrate (45.1 g), $Pd(OAc)_2$ (2.9 g, 12.92 mmol, 0.03 equiv), sodium carbonate (92 g, 868.01 mmol, 2.10 equiv), and N,N-dimethylformamide (1.25 L). The resulting solution was stirred for 12 h at 80° C. The reaction repeated four times. The reaction mixtures were combined and the solids were filtrated out. The filtrate was diluted with 10 L of brine and extracted with 3×5 L of ethyl acetate. The organic layers were combined and washed with 4×6 L of brine. The mixture was dried over anhydrous sodium sulfate and concentrated under vacuum. The residue was applied onto a silica gel column with ethyl acetate/petroleum ether (1/20). The collected fractions were combined and concentrated under vacuum. This resulted in 258 g (crude) of ethyl 2-(5-fluoro-1-benzofuran-3-yl)acetate (6) as light yellow oil.

Synthesis of Intermediate 7

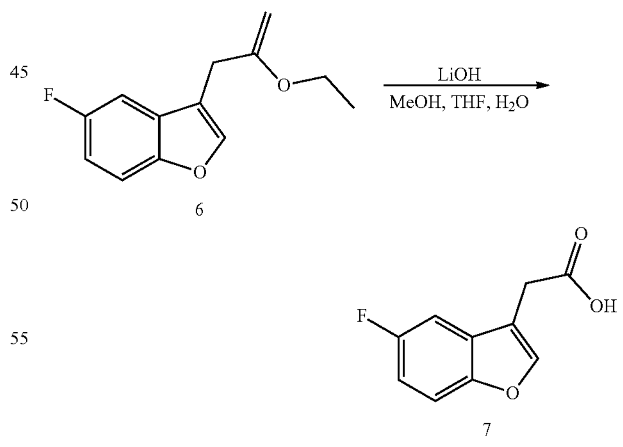

6

7

Into a 5-L round-bottom flask was placed ethyl 2-(5-fluoro-1-benzofuran-3-yl)acetate (147 g, 661.53 mmol, 1.00 equiv), methanol (1 L), tetrahydrofuran (1 L), water (1 L), and LiOH (47.7 g, 1.99 mol, 3.01 equiv). The resulting solution was stirred for 3 h at room temperature. The reaction repeated twice. The mixture was concentrated under vacuum and then extracted with 1 L of dichloromethane. The aqueous layer was collected and the pH of the layer was adjust to 1~3 by hydrogen chloride (1 mol/L). The resulting solution was extracted with 3×1 L of ethyl acetate and the combined organic layers were dried over anhydrous sodium sulfate and concentrated under vacuum. This resulted in 160 g (62%) of 2-(5-fluoro-1-benzofuran-3-yl) acetic acid (7) as a white solid.

Synthesis of Intermediate 8

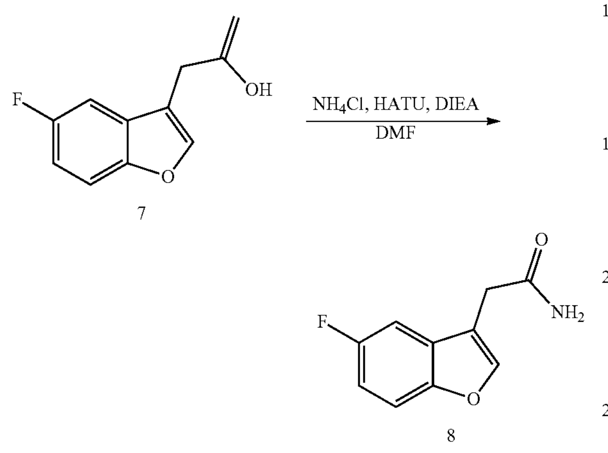

7

8

Into a 10-L round-bottom flask was placed 2-(5-fluoro-1-benzofuran-3-yl) acetic acid (160 g, 824.1 mmol, 1.00 equiv), NH4Cl (436 g, 8.16 mol, 9.89 equiv), N,N-dimethylformamide (6 L), DIEA (1064 g, 8.24 mol, 9.99 equiv), and HATU (376 g, 988.88 mmol, 1.20 equiv). The resulting solution was stirred for 12 h at room temperature. The resulting solution was diluted with 10 L of water. The solids were collected by filtration to give in 126 g (78%) of 2-(5-fluoro-1-benzofuran-3-yl) acetamide (8) as a white solid.

Synthesis of 9-ING-41 in crystalline Form I

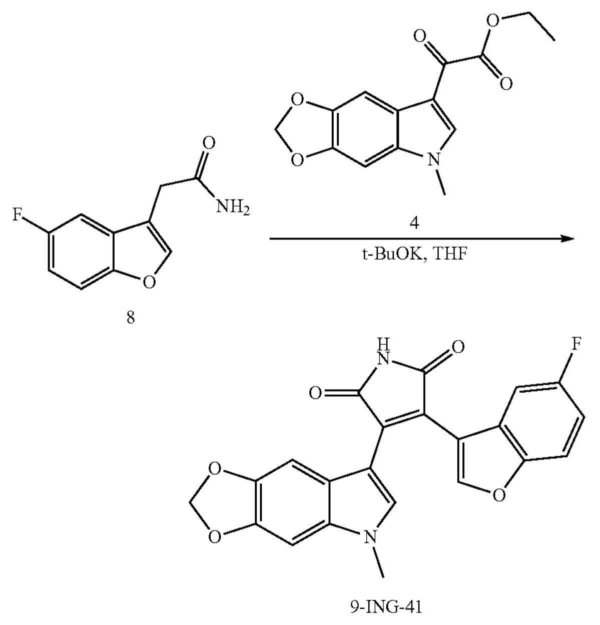

4

8

9-ING-41 t-BuOK (1200 mL, 1 mol/L in THF) was added dropwise into a solution of ethyl 2-[5-methyl-2H,3H,5H-furo[2,3-f]indol-7-yl]-2-oxoacetate (100 g, 365.9 mmol, 1.00 equiv), 2-(5-fluoro-1-benzofuran-3-yl) acetamide (72 g, 372.7 mmol, 1.02 equiv) in tetrahydrofuran (3 L) at 0° C. under nitrogen. The reaction was stirred for 2 h at room temperature. The reaction was cooled to 0° C. and poured into of 2 L of NH4Cl (saturated solution in water) and extracted with 4×2 L of dichloromethane. The organic layers were combined, dried over anhydrous sodium sulfate and concentrated under vacuum. The residue was applied onto a silica gel column with ethyl acetate/dichloromethane/petroleum ether (1/1/5). The collected fractions were combined and concentrated under vacuum to give 107.9 g (74%) of 3-(5-fluoro-1-benzofuran-3-yl)-4-[5-methyl-2H, 5H-[1,3]dioxolo[4,5-f]indol-7-yl]-2,5-dihydro-1H-pyrrole-2,5-dione as a red solid. This red solid is 9-ING-41 crystalline Form I. MS-ESI: [M+H]+=405.

Example 3: Preparation of 9-ING-41 Crystalline Form II

Crystalline Form II of 9-ING-41 was prepared by slow evaporation of a solution of 9-ING-41 as follows. 29.12 mg of 9-ING-41 (Form I) was weighed into a glass vial and 3 mL of 3-methylbutanol was added. 80.43 mg of 9-ING-41 (Form I) was weighed into a separate glass vial and 3 mL of acetone was added. The resulting suspensions were filtered, and 100 μL of each filtrate was mixed in a well of a 96-well plate. The mixture was evaporated in an operating laboratory fume hood under ambient conditions, resulting in solid 9-ING-41 crystalline form II. This material produced the XRPD shown in FIG. 1.

Example 4: Preparation of 9-ING-41 Crystalline Form II

About 100 mg 9-ING-41 Form I was weighed into a vial. 7 ml of a 10:1 (vol/vol) mixture of isoamyl alcohol:acetonitrile was added to the vial. The mixture was heated at 80° C. to give a solution which was subsequently filtered and seeded with form II 9-ING-41. The mixture was stirred while cooling to room temperature, resulting in crystallization. XRPD showed the resulting solid to be Form II.

Example 5: Preparation of 9-ING-41 Crystalline Form II

About 2.0 g Form I was weighed into vial. 150 ml of a 10:1 (vol/vol) mixture of isoamyl alcohol:acetonitrile was added to the vial. The mixture was heated at 90° C. to give a solution which was subsequently filtered and seeded with form II 9-ING-41. The mixture was stirred while cooling to room temperature, resulting in crystallization. The crystalline solid (1.46 g) was characterized by PLM, XRPD, DSC and TGA. PLM showed the crystalline solid to be irregular lump crystals. XRPD (see FIG. 2) showed the crystalline solid to be Form II. DSC showed a first endotherm with an onset temperature of 216° C., which is attributed to melting of Form II, followed by an exotherm that is attributed to Form I crystallization, followed by a second endotherm with an onset temperature of 228° C., See FIG. 3, which is attributed to Form I melting. TGA showed the form to lose about 0.4% by weight before 250° C. See FIG. 4.

Example 6. Mechanical and Pressure Effects 10.0 mg of Form II was weighed into mortar and ground for 5 min. The remaining solid was collected and analyzed by XRPD. The ground solid remained Form II 9-ING-41.

4.50 mg of Form II was compressed into tablet. The tablet was then ground into powder and analyzed by XRPD. Compression had no effect on the crystalline form.

Example 7. Thermal Treatment-Preparation of Amorphous 9-ING-41

9-ING-41 Form II was heated by DSC to the final temperature of 260° C. at the rate of 10° C./min. The melted product was put into an ice bath immediately and held for 15 minutes. The residue was analyzed by XRPD, which showed that the material was amorphous.

9-ING-41 Form II was heated to the final temperature of 260° C. at the rate of 10° C./min, then cooled down to −40° C. and re-heated to 260° C. at the same heating rate, and then cooled down to 40° C. The residue was analyzed by XRPD, which showed that the material was amorphous.

Example 8. Solubility Study—24 Hour

9-ING-41, either Form I or Form II, was added to 1 mL of each of 10 different solvents in a vial to make a suspension. The samples were shaken at 2000 rpm in a shaker at room temperature for 24 hours. Mixtures were visually examined to ensure saturation. After 24 hours, 1 mL of suspension was filtered through a 0.45 μm nylon micro-filtration membrane into another clear glass vial, respectively. The filtrate was analyzed by HPLC and the remaining solids were analyzed using XRPD. The solubility results are shown in Table 2 below.

TABLE 2

Solubility of Solid Forms of 9-ING-41

| EXP ID | Media | Form I (mg/mL) | Form II (mg/mL) |
|---|---|---|---|
| 1 | Water | Not detected | Not detected |
| 2 | EtOH | 1.273 | 0.903 |
| 3 | PEG400 | 96.522 | >100 |
| 4 | Labrasol | 60.501 | 68.455 |
| 5 | Benzyl Benzoate | 52.970 | 73.265 |
| 6 | Dimethyl Acetamide | >100 | >100 |
| 7 | Benzyl Alcohol | 24.049 | 30.553 |
| 8 | Sesame oil | — | — |
| 9 | PEG400:Tween80:EtOH (75:8:17) | 72.815 | 90.418 |
| 10 | PEG300:BzOH:Water (65:10:25) | 5.087 | 9.410 |

The remaining solids in the experiments in which Form I was the starting material remained Form I.

The remaining solids in experiments in which Form II was the starting material changed form with the exception of the water and sesame oil experiments. In the water and sesame oil experiments, the remaining solids were Form II. In the ethanol experiment, the remaining solids were a solvate. In the other experiments, the solids appeared to be Form I.

Example 9. Solubility Study—1 Hour

Step 1: A sufficient amount of Form I was added to 1 mL solvent (EtOH, Labrasol, Benzyl Benzoate, Benzyl Alcohol, PEG400:Tween80:EtOH (75:8:17) and PEG300:BzOH:Water (65:10:25)) to make a suspension. The samples were shaken at 2000 rpm in a shaker at room temperature for 24 hours.

Step 2: The vials were visually examined to ensure saturation. 1 mL of suspension was filtered at 24 hours through a 0.45 μm nylon micro-filtration membrane into another clean clear glass vial. The filtrate was analyzed by HPLC.

Step 3: Excess Form II was added to the 6 residual filtrates from Step 2 to make a suspension, respectively. The samples were shaken at 2000 rpm in a shaker for 1 hour. The suspensions were filtered after 1 hour through a 0.45 μm nylon micro-filtration membrane into another clean glass vial. The filtrate was analyzed by HPLC and the remaining solids were analyzed using XRPD.

TABLE 3

Solubility of Solid Forms of 9-ING-41

| EXP ID | Media | Form I (mg/mL) | Form II (mg/mL) |
|---|---|---|---|
| 1 | EtOH | 1.257 | 2.547 |
| 2 | Labrasol | 61.370 | 86.953 |
| 3 | Benzyl Benzoate | 48.313 | 71.808 |
| 4 | Benzyl Alcohol | 22.308 | 39.869 |
| 5 | PEG400:Tween80:EtOH (75:8:17) | 73.421 | 106.140 |
| 6 | PEG300:BzOH:Water (65:10:25) | 4.959 | 10.238 |

The remaining solids in Labrasol, Benzyl Benzoate, Benzyl Alcohol, and PEG400:Tween80:EtOH (75:8:17) were Form I, showing that the solid Form II rapidly converts to Form I. The crystal form of remaining solids did not change in EtOH and PEG300:BzOH:Water (65:10:25).

Example 10. Solubility in Sesame Oil

The solubility of 9-ING-41 in sesame oil cannot be measured by HPLC. The solubility was estimated by adding weighed portions of Form I (or Form II) into sesame oil. The samples were stirred for 24 hours at room temperature and the vials were visually examined to ensure dissolution. Solid was added in this manner until added solid did not dissolve in 24 hours. The results are shown in Table 4 below.

TABLE 4

The solubility results of sesame oil

| EXP ID | Raw material | Weight (mg) | Sesame oil Weight (mg) | visual result | Estimated solubility |
|---|---|---|---|---|---|
| 1 | Form I | 1.00 | 3464.12 | Incomplete dissolution | 0.167-0.289 μg/mg |
| 2 | Form I | 1.00 | 5997.92 | dissolution | |
| 3 | Form II | 0.90 | 1214.50 | dissolution | 0.741-1.21 μg/mg |
| 4 | Form II | 3.18 | 2638.01 | Incomplete dissolution | |

The invention claimed is:

1. A method of treating cancer in a patient comprising administering to a patient in need thereof a therapeutically effective amount of a pharmaceutical composition comprising a pharmaceutically acceptable excipient, and a solid form of 3-(5-fluorobenzofuran-3-yl)-4-(5-methyl-5H-[1,3]dioxolo[4,5-f]indol-7-yl)pyrrole-2,5-dione characterized by an X-ray powder diffraction pattern comprising peaks at three or more of 7.8, 12.9, 15.8, 18.1, 18.9, 19.5, 22.1, 22.7, 28.0, and 28.5, ±0.2 degrees 2-theta, on the 2-theta scale with lambda=1.54 angstroms (Cu Kα).

2. The method of claim 1, wherein the cancer is brain, lung, breast, ovarian, bladder, neuroblastoma, renal, or pancreatic cancer.

3. The method of claim 1, wherein the pharmaceutical composition is in a dosage form that is a tablet, capsule, caplet, reconstitutable powder, elixir, liquid, colloidal or other types of suspension, emulsion, beads, beadlets, granules, microparticles, nanoparticles, or combinations thereof.

4. The method of claim 3, wherein the pharmaceutical composition is in a dosage form that is a tablet.

5. The method of claim 3, wherein the pharmaceutical composition is in a dosage form that is a capsule.

6. The method of claim 3, wherein the pharmaceutical composition is in a dosage form that is a caplet.

7. The method of claim 3, wherein the pharmaceutical composition is in a dosage form that is a reconstitutable powder.

8. The method of claim 3, wherein the pharmaceutical composition is in a dosage form that is a liquid.

9. The method of claim 3, wherein the pharmaceutical composition is in a dosage form that is a suspension.

10. A method of treating traumatic brain injury in a patient comprising administering to a patient in need thereof a therapeutically effective amount of a pharmaceutical composition comprising a pharmaceutically acceptable excipient, and a solid form of 3-(5-fluorobenzofuran-3-yl)-4-(5-methyl-5H-[1,3]dioxolo[4,5-f]indol-7-yl)pyrrole-2,5-dione characterized by an X-ray powder diffraction pattern comprising peaks at three or more of 7.8, 12.9, 15.8, 18.1, 18.9, 19.5, 22.1, 22.7, 28.0, and 28.5, ±0.2 degrees 2-theta, on the 2-theta scale with lambda=1.54 angstroms (Cu Kα).

11. The method of claim 10, wherein the pharmaceutical composition is in a dosage form that is a tablet, capsule, caplet, reconstitutable powder, elixir, liquid, colloidal or other types of suspension, emulsion, beads, beadlets, granules, microparticles, nanoparticles, or combinations thereof.

12. The method of claim 11, wherein the pharmaceutical composition is in a dosage form that is a tablet.

13. The method of claim 11, wherein the pharmaceutical composition is in a dosage form that is a capsule.

14. The method of claim 11, wherein the pharmaceutical composition is in a dosage form that is a caplet.

15. The method of claim 11, wherein the pharmaceutical composition is in a dosage form that is a reconstitutable powder.

16. The method of claim 11, wherein the pharmaceutical composition is in a dosage form that is a liquid.

17. The method of claim 11, wherein the pharmaceutical composition is in a dosage form that is a suspension.

* * * * *